US006829957B2

(12) United States Patent
Lee, Jr. et al.

(10) Patent No.: US 6,829,957 B2
(45) Date of Patent: Dec. 14, 2004

(54) APPARATUS AND METHODS FOR DETERMINING SELF-WEIGHT CONSOLIDATION AND OTHER PROPERTIES OF MEDIA

(75) Inventors: Landris T. Lee, Jr., Vicksburg, MS (US); Daniel A. Leavell, Vicksburg, MS (US); Mickey D. Blackmon, Vicksburg, MS (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 337 days.

(21) Appl. No.: 10/118,012

(22) Filed: Apr. 9, 2002

(65) Prior Publication Data

US 2003/0188590 A1 Oct. 9, 2003

(51) Int. Cl.[7] .............................................. G01N 33/00
(52) U.S. Cl. ...................................................... 73/866
(58) Field of Search .......................... 73/866.4, 865.6, 73/866, 39, 819, 73, 864, 864.51, 864.53

Primary Examiner—Robert Raevis
(74) Attorney, Agent, or Firm—Earl H. Baugher, Jr.

(57) ABSTRACT

Provided is a consolidometer and methods of its use. In its preferred embodiment, the device and methods permit accurate and convenient laboratory sampling of the self-weight consolidation of media, such as soft soil and soil slurries that may result from dredging operations. One option also provides for attaching sensors at locations along the consolidometer for taking data on additional characteristics of the media.

20 Claims, 4 Drawing Sheets

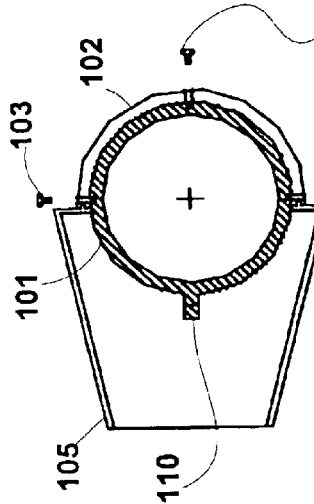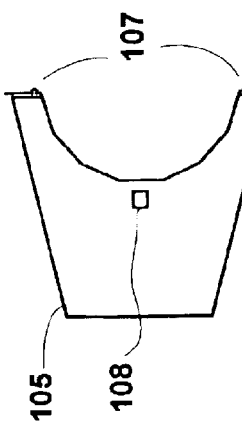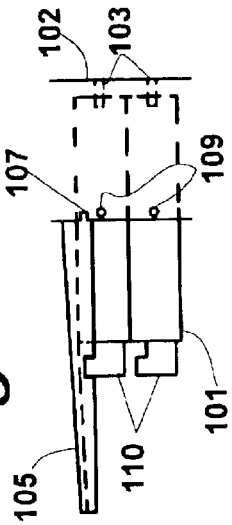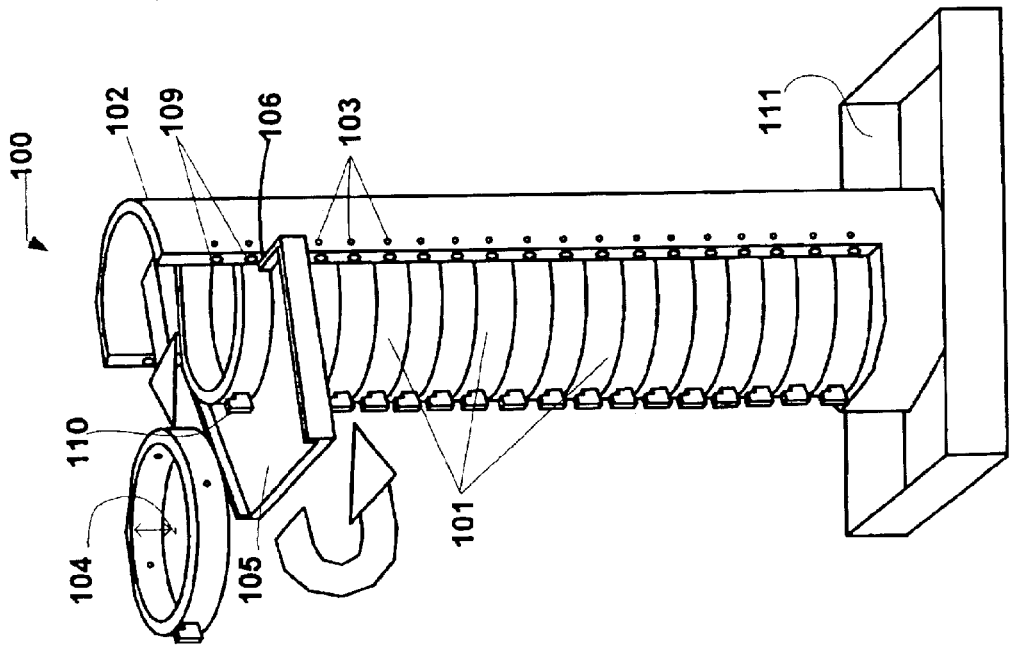

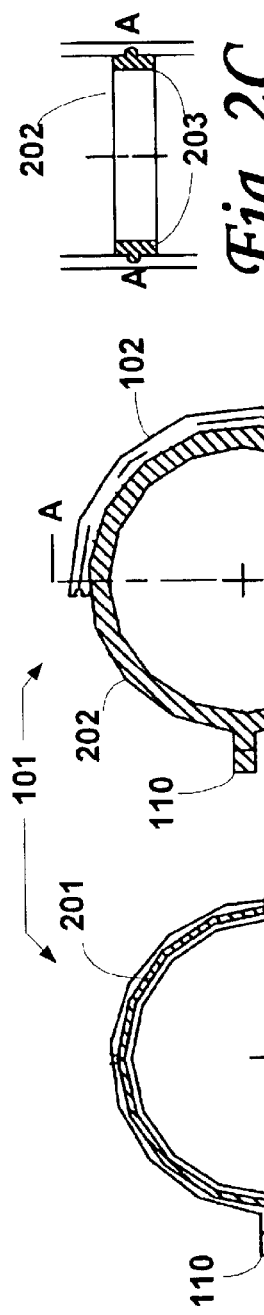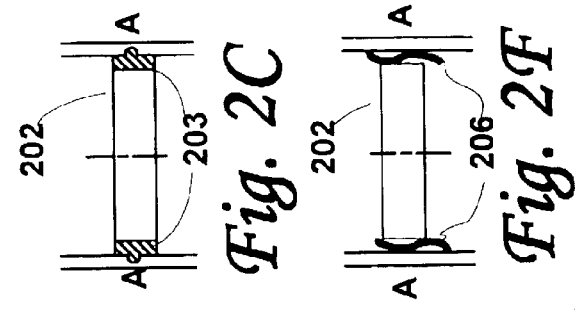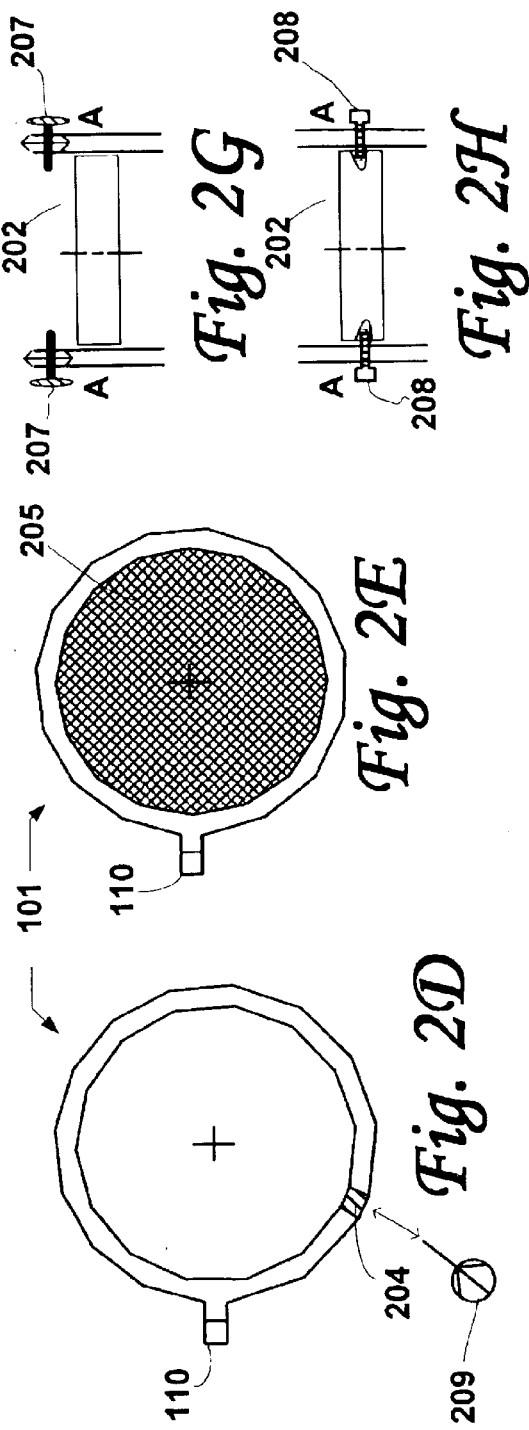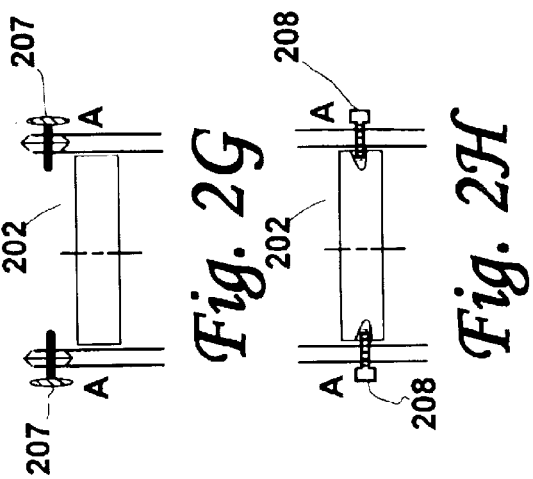

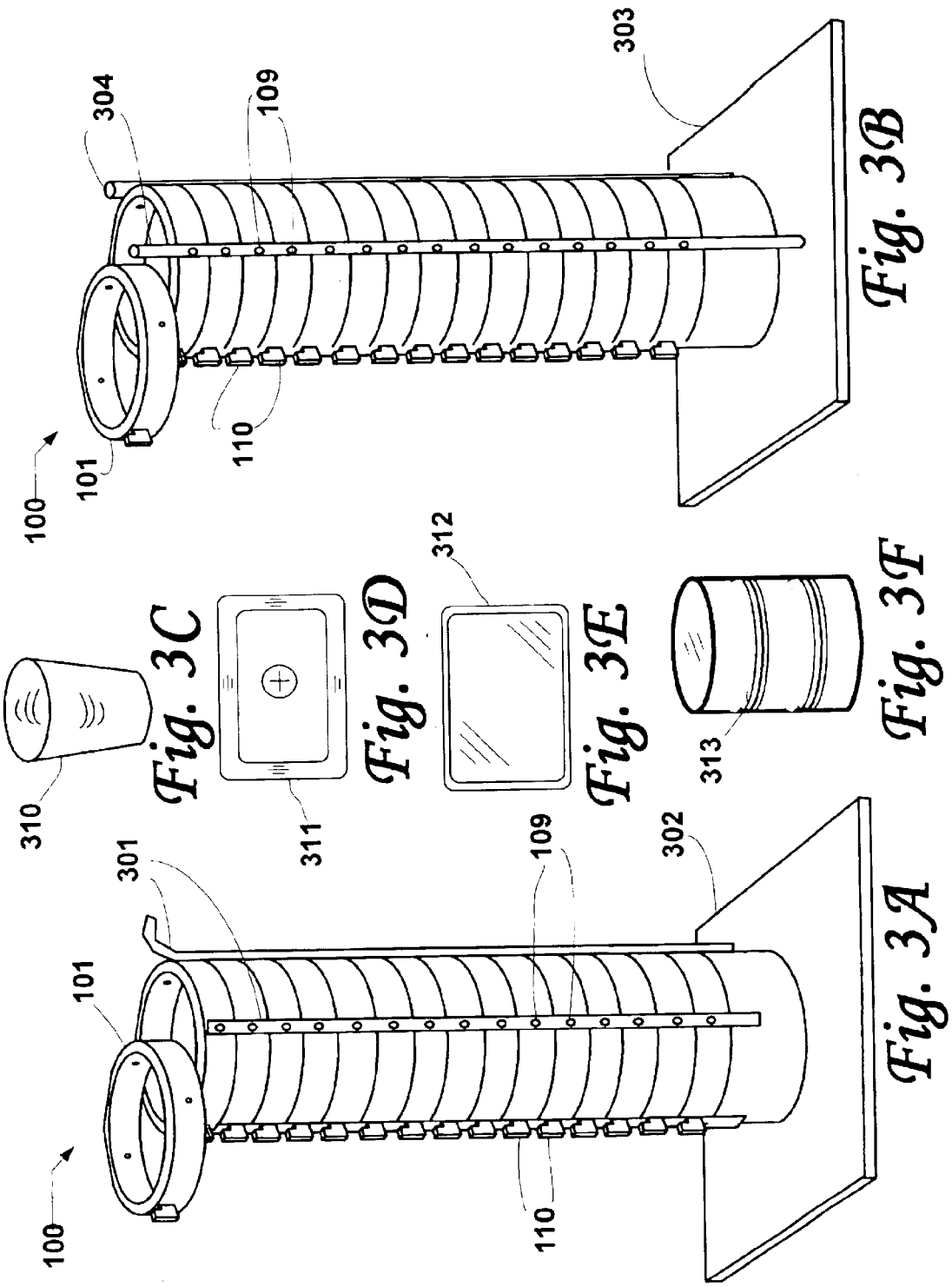

APPARATUS AND METHODS FOR DETERMINING SELF-WEIGHT CONSOLIDATION AND OTHER PROPERTIES OF MEDIA

STATEMENT OF GOVERNMENT INTEREST

Under paragraph 1(a) of Executive Order 10096, the conditions under which this invention was made entitle the Government of the United States, as represented by the Secretary of the Army, to the entire right, title and interest in any patent granted thereon by the United States. This and related patents are available for licensing. Please contact Phill Stewart at 601 634-4113.

BACKGROUND

The field of the invention is laboratory evaluation and geo-technical testing of media, in particular an apparatus and methods of its use for evaluation of soft soils or soil slurry materials.

Consolidation testing of soft soil or slurry materials using traditional geo-technical testing methods and equipment is not practically possible, but predicting the consolidation behavior of such materials is of paramount importance in designing for dredged material or mine waste disposal operations, for example. During laboratory self-weight consolidation for modeling the field behavior of media such as dredged or other slurry material, the material undergoes significant strain as pore fluid drains and the media particles compact in the mix. Such strain behavior is modeled differently from that of traditional consolidation behavior. Traditionally, self-weight consolidation is assumed to be negligible and the change in void ratio is assumed to vary directly with the change in the specimen (column) height. Needed is a device and method that overcomes limitations of traditional consolidation testing by allowing self-weight consolidation to freely occur and by enabling determination of void ratio changes directly from tests of the sampled media contained inside each insert in a stack (column).

The only known means of characterizing discrete layer properties of a soft soil material has heretofore been accomplished using a method in which each ring is accessed by moveably sliding an enveloping outer shell in a downward direction. The moveable outer shell has contributed to difficulties in accomplishing accurate specimen testing by unduly disrupting the self-consolidation process, and often impinges on the inner rings.

A preferred embodiment of the present invention enables practical laboratory testing of soft soils and slurries to be accomplished, while validating large strain consolidation theory assumptions.

SUMMARY

A consolidometer for determining properties of media, in particular, self-weight consolidation, is provided. As well as solids, the media include fluids incorporating suspended or dissolved solids. It uses inserts that are placed in a stacked configuration in a longitudinal frame, generally set vertically on its base in a containment device. The frame supports the inserts, typically rings, such that any media under investigation is contained wholly within the interior volumes of the inserts, e.g., the annular volume of the stack of ring inserts. The frame may be a cylinder cut in half lengthwise to permit insertion and withdrawal of said ring inserts at locations along its length. Also provided is a collection device, typically a flat tray configured to abut and secure onto any one of the ring inserts and with bosses to fit recesses in the frame. It is used seriatim with the insert rings to collect samples along the length of the media column. The ring inserts are secured to the frame in any of a number of ways, a typical method using one or more set screws for each ring insert. When a sample is taken, the set screws are removed and the ring insert slid out of the stack. Optionally, sensors may be inserted in one or more ring inserts to take additional data on the column of media.

Also provided is a method for determining properties of media, in particular, self-weight consolidation properties. Using a consolidometer that represents a preferred embodiment of the present invention, one fills the stacked inserts of the consolidometer with the media to be evaluated and allows the mediate to self-consolidate. The topmost inserts that no longer contain media are removed. Then, a sample collection device, such as a specially-configured flat tray, is attached to the topmost insert having media contained in its interior volume. The set screws, or other retaining devices, are removed from the insert and the insert is slid from its position on top of the stack out over the flat sample tray. By removing the insert the media contained therein is dropped onto the flat tray for subsequent transfer to a sample vial or like container. The process is then repeated for each insert in the stack. Optionally, one or more of the inserts may be fitted with one or more sensors that provide additional information about the media at that point in the stack, based on a pre-specified data collection protocol.

Advantages of a preferred embodiment of the present invention include:

higher accuracy of laboratory sampling by conducting sampling and testing at discrete spatial intervals;

adaptable to various types of geo-technical test and evaluation;

ease of taking samples with reduced spillage;

multiple laboratory functions able to be provided with a given configuration;

low skill level needed for operators implementing the methods of use;

low cost of the capital equipment needed to implement;

low maintenance cost of the capital equipment; and low overall cost to implement including cost of necessary supplemental fabrication material.

A preferred embodiment of the present invention overcomes traditional geo-technical testing constraints encountered in laboratory investigations of soft soils or soil slurries because the invention allows for material sampling, material testing, and evaluation of material characteristics during the specimen's self-weight consolidation process. This enables accurate laboratory representation and modeling of soft soil or slurry self-weight consolidation processes occurring during dredged material disposal, mine tailing operations, or other soft sediment placement scenarios.

BRIEF DESCRIPTION OF DRAWINGS

FIG. 1A is a rendering of an embodiment of the present invention in use.

FIG. 1B is a top view of one of the stacked inserts connected to a sampling tray.

FIG. 1C is a top view of a sampling tray and its pertinent parts.

FIG. 1D is a cross-sectional view of how a sampling tray fits to an embodiment of the present invention to permit taking individual samples within the vertical column.

FIG. 2A is a top view of a stacked ring insert with a groove for an O-ring.

FIG. 2B is a top view of a stacked ring insert with a rail for mounting in a track of a structure.

FIG. 2C is a view of a cross-section at A—A through FIG. 2B.

FIG. 2D is a top view of a stacked ring insert with an outlet for installation of a sensor or transducer.

FIG. 2E is a top view of a stacked ring insert with a screen for performing specialized self-weight consolidation testing.

FIG. 2F is a view of a cross-section at A—A through FIG. 2B, replacing the ring groove and rail with spring clips.

FIG. 2G is a view of a cross-section at A—A through FIG. 2B, replacing the ring groove and rail with slidable clamps.

FIG. 2H is a view of a cross-section at A—A through FIG. 2B, replacing the ring groove and rail with bolts threaded into the sides of the stacked inserts.

FIG. 3A is a profile of an embodiment of the present invention that uses a flexible mount attached to a base as structure for mounting stacked inserts.

FIG. 3B is a profile of an embodiment of the present invention that uses a rigid mount attached to a base as structure for mounting stacked inserts.

FIG. 3C is a profile of a bucket used to collect liquid from an embodiment of the present invention.

FIG. 3D is a top view of a sink used to collect liquid from an embodiment of the present invention.

FIG. 3E is a top view of a pan used to collect liquid from an embodiment of the present invention.

FIG. 3F is a profile of a barrel used to collect liquid from an embodiment of the present invention.

DETAILED DESCRIPTION

Figure 4:
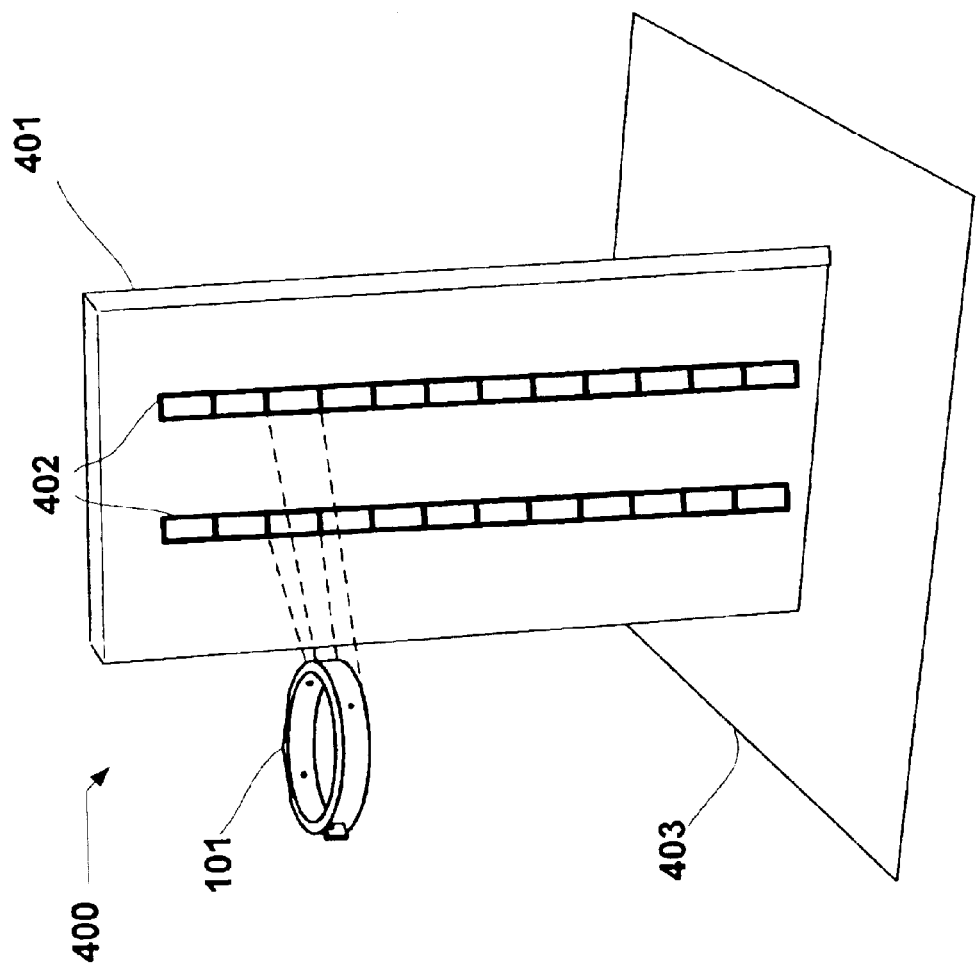
FIG. 4 depicts an embodiment of the present invention that uses a flat panel for supporting the stacked inserts.

A preferred embodiment of the present invention provides laboratory methods and devices for evaluation and geo-technical testing of media, such as soft soil or soil slurry materials, that are being investigated after self-weight consolidation.

The soft soil or slurry is placed inside the stacked inserts 101 of the consolidometer 100 and allowed to consolidate under its own weight. Consolidation occurs as the pore fluid drains out of the soil matrix and the soil particles achieve an interlocking pattern at resists further consolidation. Since the soil sample remains constrained inside the stacked inserts 101, e.g., the volume may comprise a series of stacked cylinders, each cylinder's volume defined via one of the stacked inserts 101, typically rings as shown in FIG. 1A, the complete series of stacked inserts 101 comprising a sample column, essentially one-dimensional consolidation occurs, i.e., vertical consolidation. The soil's geo-technical properties may be determined in discrete vertical intervals by serially removing the stacked inserts 101, e.g., rings, collecting the media, typically soil, from each insert 101, and preserving the sample for further geo-technical soil testing as required.

EXAMPLE I

Refer to FIGS. 1A-1D. A consolidometer 100 supports a column of stacked ring inserts 101. In this embodiment, the structure 102 has a semi-circular shape for both its inner and outer sides to accommodate insertion and removal of the circular ring inserts 101. The structure 102 and ring inserts 101 may be constructed of PLEXIGLAS™, or other transparent material, to enable visual recording of the self-weight consolidation process that is not possible using traditional methods and equipment. Further, the shape of the structure 102 and insert rings 101 shown in FIG. 1A is not required. Indeed, any polygon shape may be used so long as the inserts 101 are matched to the shape of the structure 102. Refer to FIGS. 3A and 3B. FIG. 3A depicts flexible hold-downs 301 attached to a base 302. FIG. 3B depicts rigid hold-downs 304 attached to a base 303. Even a flat panel configuration 400 as shown in FIG. 4 may be used as the support structure provided the stackable inserts 101 have a flat side (not shown separately) or sealing O-rings 201 between them with suitable interfacing means 402, such as spring clips 206 to the panel 401. The panel 401 may be appropriately supported on a plate 403 via any of a number of attachment means such as welding, epoxy, or mechanical fasteners (not shown separately). Each ring insert 101 is vertically stacked into position against the structure 102, each ring insert 101 individually affixed to the structure 10 such as with set screws 103, rail 202 in FIG. 2B and slotted track 203 in FIG. 2C, bolts 208 FIG. 2H, slidable clamps 207 in FIG. 2G, spring clips 206 in FIG. 2F, or other methods of temporary attachment.

The media, typically soil or slurry material, occupies the space 104 in each ring insert 101 that defines the volume of each sample that may be taken and thus forms a continuous column, wholly contained within the insert rings 101, whose total height depends on the total number of stacked inserts 101, and whose height may precisely match that of the modeled in situ material "column." As the media consolidates, the uppermost inserts 101 will lose media by subsidence, and the interface boundary between any pore fluid and media particles gradually moves down the column. At a selected time, most likely at the end of the media's primary consolidation period, remaining pore fluid with minimal amounts of media particles is drained, and all empty inserts 101 are disengaged from the structure 102, removed, and laid aside. The contents of the uppermost insert 101 that contains media may be sampled by first removing the constraints on the insert, typically set screws 103. A sample collection device, typically a specially configured flat plate collector 105, is positioned on the insert 102. Next, the insert 101 is disengaged from the structure 102, slowly removed by grasping the insert pull tab 110, and sliding the insert 101 outward horizontally. Once the insert 101 is free of the structure 102, its contents are deposited on the flat plate 105 by lifting the insert 101 vertically from the flat plate collector 105.

The collection plate 105 attaches to the structure 102 at designated points 106 and provides a smooth surface onto which an outwardly-sliding insert 101 releases its contents. The collection plate 105 consists of a horizontal surface with protruding bosses 107 and a pull tab receptor 108 located on the underside of the collection plate 105 at the same end of the collection plate 105 as the bosses 107. To affix the collection plate 105 at each insert 101, the bosses 107 are inserted into openings 109 located on the outer flange of the structure 102, and the pull tab receptor 108 is positioned over and mated to a pull tab 110. The collection plate 105 is disengaged from the insert 101 and structure 102 by lifting the collection plate 105 up and away from the pull tab receptor 109 while pulling horizontally away from the structure 102. This disengages the bosses 107 from he recesses 109.

The process is repeated for each successive insert 101 in the column of inserts 101. At the conclusion of sampling, no inserts 101 remain attached to the structure 102. The consolidometer 100 is cleaned of any remaining media and setup for future tests.

EXAMPLE II

Refer to FIG. 2E. Another embodiment of the method and apparatus provides for specimen testing that conforms to one-dimensional large strain consolidation theory for singly-drained specimens. Replacing the bottom insert 101 with a porous late 205 permits shorter-duration consolidation that conforms to one-dimensional large strain consolidation theory for doubly-drained specimens. To further facilitate this shorter-duration consolidation, various means to collect liquid may be employed by placing the consolidometer upon these means. These include means such as a bucket 310 in FIG. 3C, a sink in FIG. 3D, a pan in FIG. 3E, a barrel in FIG. 3F or an integral pan 111 as shown in FIG. 1A. Doubly-drain testing models a field site where, for example, dredged material is placed directly on a coarse-grained foundation allowing free drainage through the bottom of the dredged material.

EXAMPLE III

Yet another embodiment may be used to obtain geotechnical information in addition to self-weight consolidation values. Refer to FIG. 2D. Each insert 101 may be tapped or provided with an opening or outlet 204 to attach a sensor or transducer 209. For example, pore fluid pressure sensors (not separately shown) may be attached to obtain pore fluid pressure variations during the consolidation process. Density measurements of the specimen as a function of column height may be made by attachment of suitable sensors 209 on or about the periphery of either the structure 102 or the inserts 101. The consolidometer 100 may be converted readily to enable traditional consolidation testing by adding an external loading device (not separately shown) capable of controlled displacement or controlled load increment. Refer to FIG. 2A. Further, the column may be made fluid tight with he addition of O-rings in the slots 201 shown.

With such adaptation, a preferred embodiment of the present invention enables consolidation behavior testing throughout the entire range of a material's plausible pore fluid content. For example, the consolidation characteristics for a dredged material may be determined for its expected life cycle void ratio range from a suspended sediment state to a fully consolidated state, without the use of additional geo-technical testing equipment such as an oedometer.

Although specific functions for consolidometers and methods of their use as multiple instruments are discussed, such as self-weight consolidation measurements and consolidation behavior testing, this does not exclude other functions using the described apparatus and method from falling within the ambit of the claims herein.

We claim:

1. A method for determining self-weight consolidation properties of media, comprising:
    providing a consolidometer, comprising:
        inserts circumscribing an interior volume thereto;
        at least one frame, having an interior and exterior dimension and two ends, one said end serving as base and the other said end capable of being at least partially open, said frame having a length much greater than other dimensions of said frame,
    wherein said frame supports said inserts in a stacked configuration such that said media is contained wholly within said interior volumes of said inserts, and
    wherein said frame permits insertion and withdrawal of said inserts at locations along said length of said frame;
    a collection device suitable for affixing to said inserts;
    filling said consolidometer with media to be evaluated, wherein said media is allowed to self-consolidate;
    thereafter removing said topmost inserts for which said interior volume therewith associated contains no said media;
    attaching said collection device to a first topmost insert having its interior volume at least partially filled with said media;
    removing said first topmost insert from said consolidometer, wherein said media encompassed by said first topmost insert is transferred to said collection device;
    transferring said transferred media to a container; and
    attaching said collection device to each remaining said insert in said consolidometer and removing each said remaining insert from said consolidometer sequentially from said first topmost insert to said base of said consolidometer, thereby depositing said media from said interior volume of said removed insert into said collection device at each said removal,
wherein a sample is taken and may be stored in for each insert for which said media is deposited into said collection device.

2. A consolidometer for determining self-weight consolidation properties of media, comprising:
    inserts circumscribing an interior volume thereto;
    at least one frame, having an interior and an exterior dimension and two ends, one said end serving as a base and the other said end having an opening, said frame having a length much greater than other dimensions of said frame,
wherein said frame supports said inserts in a stacked configuration such that said media is contained wholly within said interior volumes of said inserts; and wherein said frame permits insertion and withdrawal of said inserts at locations along said length of said frame; and
    at least one collection device that suitable for affixing to said inserts.

3. The consolidometer of claim 2 further comprising a containment apparatus in proximity to said base of said frame, said containment apparatus selected from the group consisting essentially of: a pan, a bucket, sink, a drum, a container integral with said base, and any combinations thereof.

4. The consolidometer of claim 2 in which said outside dimension of each said inserts permit a close fit of said inserts with at least part of said interior dimension of said frame, wherein said interior dimension is that interior perimeter of a cross section taken along said length of said frame.

5. The consolidometer of claim 2 in which said inserts are affixed to said frame to prevent unintentional movement thereafter.

6. The consolidometer of claim 5 in which said inserts are affixed by a means selected from the group consisting of: set screws, bolts, slotted tracks, slidable clamps, spring clips, and any combinations thereof.

7. The consolidometer of claim 2 in which said frame may be of an interior dimension configuration selected from the group consisting of: a semi-circle, a polygon, and a flat panel.

8. The consolidometer of claim 2 in which at least one of said inserts is configured with at least one sensor.

9. A consolidometer for determining self-weight consolidation properties of media, comprising:

rings, wherein each said ring circumscribes a volume that may be approximated by a cylinder;

at least one frame, having an interior semi-circular dimension and an exterior dimension and two ends, one said end serving as a base and the other said end having an opening, said frame having a length much greater than other dimensions of said frame, wherein said frame supports said rings in a stacked configuration such at said media is contained wholly within said circumscribed volumes of said rings; and wherein said frame permits insertion and withdrawal of said rings at locations along said length of said frame; and at least one sampling tray that may be affixed to said consolidometer.

10. The consolidometer of claim 9 further comprising a containment apparatus in proximity to said base of said frame, said containment apparatus selected from the group consisting essentially of: a pan, a bucket, a sink, a drum, a container integral with said base, and any combinations thereof.

11. The consolidometer of claim 9 in which said outside dimension of each said rings permit a close fit of said rings with said semi-circular interior dimension of said frame, wherein said semi-circular interior dimension is that interior perimeter of a cross section taken along said length of said frame.

12. The consolidometer of claim 9 in which said rings are affix to said frame to prevent unintentional movement thereafter.

13. The consolidometer of claim 12 in which said rings are affixed by a means selected from the group consisting of: set screws, bolts, slotted tracks, slidable clamps, spring clips, and any combinations thereof.

14. The consolidometer of claim 9 in which each said ring has at least one pull tabs for facilitating removal of said rings from said frame.

15. The consolidometer of claim 14 in which said sampling tray is configured to follow at least part of said outside dimension of said ring and notched to fit over said at least one pull tab, wherein said sampling tray configuration facilitates transfer of said media to said sampling tray upon removal of a ring from said frame.

16. The consolidometer of claim 9 in which said sampling tray is fitted with at least one boss.

17. The consolidometer of claim 16 in which said frame is configured with recesses for receiving said at least one bosses of said sampling tray.

18. The consolidometer of claim 13 in which said rings are secured to said frame via at least one setscrew.

19. The consolidometer of claim 9 in which at least one of said rings is configured with at least one sensor.

20. A method for determining properties of media, comprising:

providing a laboratory instrument, comprising:
inserts circumscribing an interior volume thereto;
at least one frame, having an interior and an exterior dimension and two ends, one said end serving as a base and the other said end capable of being at least partially open, said frame having a length much greater than other dimensions of said frame, wherein said frame supports said inserts in a stacked configuration such that said media is contained wholly within said interior volumes of said inserts, and wherein said frame permits insertion and withdrawal of said inserts at locations along said length of said frame;
a collection device that is attachable to said inserts; and
at least one sensor, wherein said at least one sensor measures at least one characteristic of said media at pre-specified locations and pre-specified times;

filling said consolidometer with media to be evaluated;

thereafter removing said topmost inserts for which said interior volume therewith associated contains no said media;

attaching said collection device to a first topmost insert having its interior volume at least partially filled with said media;

removing said first topmost insert from said consolidometer, wherein said media encompassed by said first topmost insert is transferred to said collection device;

transferring said transferred media to a container; and attaching said collection device to each remaining said insert in said consolidometer and removing each said remaining insert from said consolidometer sequentially from said first topmost insert to said base of said consolidometer, thereby depositing said media from said interior volume of said removed insert into said collection device at each said removal, wherein a sample is taken and may be stored in a container for each insert that deposits said media into said collection device.

* * * * *